(12) United States Patent
Cooper et al.

(10) Patent No.: US 7,355,057 B1
(45) Date of Patent: Apr. 8, 2008

(54) LIQUID TRANSITION METAL ACETYLIDE CHROMOPHORES

(76) Inventors: Thomas M. Cooper, 1336 Kercher St., Miamisburg, OH (US) 45342; Benjamin C. Hall, 2964 Themmes Ct. #112, Fairborn, OH (US) 45324; Aaron R. Burke, 2400 Old Derby Ct., Vandalia, OH (US) 45377; Paul A. Fleitz, 3962 Applewood La., Dayton, OH (US) 45429

( * ) Notice: Subject to any disclaimer, the term of this patent is extended or adjusted under 35 U.S.C. 154(b) by 224 days.

(21) Appl. No.: 10/989,864

(22) Filed: Nov. 17, 2004

(51) Int. Cl.
 *C07F 15/00* (2006.01)
(52) U.S. Cl. .......................... 556/16; 556/13; 528/398; 528/487
(58) Field of Classification Search ................ 528/398, 528/487; 556/16, 13
See application file for complete search history.

(56) References Cited

U.S. PATENT DOCUMENTS

| | | | |
|---|---|---|---|
| 4,879,479 | A | 11/1989 | Frazier et al. |
| 5,698,048 | A | 12/1997 | Friend et al. |

OTHER PUBLICATIONS

Cooper et al, Glass forming liquid platinum acetyildes, Chemistry of Materials (Jul. 29, 2004), 16(17), 3215-3217; Chem Abstract 141: 277704.*
Bruce, M. I.; Davy, J.; Hall, B. C.; Jensen van Galen, Y.; Skelton, B. W.; White, A. H. "Some platinum(II) complexes derived from aromatic alkynes," *Appl. Organomet. Chem.* 2002, 16, 559-568.
Kohler, A.; Wilson, J. S.; Friend, R. H.; Al-Suti, M. K.; Khan, M. S.; Gerhard, A.; Bassler, H "The singlet-triplet energy gap in organic and Pt-containing phenylene ethynylene polymers and monomers." *J. Chem. Phys.* 2002, 116, 9457-5463.
George, R. D.; Snow, A. W. "Phthalocyanine Glasses." *Chem. Matls.* 1994, 6, 1587-1588.
Liu, Y.; Jiang, S.; Glusac, K. D.; Powell, D. H.; Anderson, D. F.; Schanze, K. S. "Photophysics of Monodisperse Platinum-Acetylide Oligomers: Delocation in the Singlet and Triplet Excited States," *J. Amer. Chem. Soc.* 2002, 124, 12412-12413.
McKay, T. J.; Bolger, J. A.; Staromlynska, J.; Davy, J. R. "Linear and nonlinear optical properties of platinum-ethynyl." *J. Chem. Phys.* 1998, 108, 5537-5541.
Rogers, J. E.; Cooper, T. M.; Fleitz, P. A.; Glass, D. J.; McLean, D. G. "Photophysical Characterization of a Series of Platinum(II)-Containing Phenyl-Ethynyl Oligomers." *J. Phys. Chem. A* 2002, 106, 10108-10115.
Emmert, L. A.; Choi, W.; Marshall, J. A.; Yang, J.; Meyer, L. A.; Brozik, J. A. "The Excited-State Symmetry Characteristics of Platinum Phenylacetylene Compounds." *J. Phys. Chem. A* 2003, 107, 11340-11346.

* cited by examiner

*Primary Examiner*—Duc Truong
(74) *Attorney, Agent, or Firm*—AFMCLO/JAZ; Bart S. Hersko

(57) ABSTRACT

The present invention relates to a series of platinum acetylide nonlinear optical chromophores which are liquid at room temperature. The viscosity of these liquid chromophores is low enough that they are easily processable into optical cells and can be used for nonlinear optical applications. The compounds remain liquids below room temperature, converting to a glass in the range of from about −80° C. to −100° C. Neat liquids have a high chromophore concentration (~1 Mole/liter) making possible the development of optical devices requiring materials with a high chromophore concentration.

5 Claims, 3 Drawing Sheets

The differential scanning calorimeter thermogram of compound 2.

The differential scanning calorimeter thermogram of compound 2.

The differential scanning calorimeter thermogram of compound 3.

The ground state absorption spectrum of compound 3 and PE2.

The triplet state absorption spectrum of compound 3 and PE2.

The triplet state absorption spectrum of neat liquid compound 3 compared to compound 3 dissolved in benzene.

The phosphorescence spectrum of compound 3 in a glassy state compared with phosphorescence spectrum of PE2 dissolved in a MeTHF glass.

LIQUID TRANSITION METAL ACETYLIDE CHROMOPHORES

The invention described herein may be manufactured and used by or for the Government of the United States for all governmental purposes without the payment of any royalty.

BACKGROUND OF THE INVENTION

The present invention relates to the field of devices for nonlinear optics, frequency conversion, optical switching, photoconductivity, photovoltaics, electroluminescence, pressure-sensitive paint and electrochemical sensor using organometallic materials. More particularly, the invention pertains to a series of platinum acetylide nonlinear optical chromophores which are liquid at room temperature.

There has been considerable interest in the synthesis, spectroscopy, nonlinear optics and structure-property relationships of transition metal acetylides. (See e.g., Rogers, J. E.; Cooper, T. M.; Fleitz, P. A.; Glass, D. J.; McLean, D. G. *J. Phys. Chem. A* 2002, 106, 10108-10115; Cooper, T. M. In *Encyclopedia of Nanomaterials and Nanotechnology*; Nalwa, H. S., Ed.; American Scientific Publishers, 2004; Vol. 10, 447-470; Liu, Y.; Jiang, S.; Glusac, K. D.; Powell, D. H.; Anderson, D. F.; Schanze, K. S. *J. Amer. Chem. Soc.* 2002, 124, 12412-12413; Kohler, A.; Wilson, J. S.; Friend, R. H.; Al-Suti, M. K.; Khan, M. S.; Gerhard, A.; Bassler,H. *J. Chem. Phys.* 2002, 116, 9457-9463; Bruce, M. I.; Davy, J.; Hall, B. C.; Jansen van Galen, Y.; Skelton, B. W.; White, A. H. *Appl. Organomet. Chem.* 2002, 16, 559-568; Szafert, S.; Gladysz, J. A. *Chem. Rev.* 2003, 103, 4175-4205; Emmert, L. A.; Choi, W.; Marshall, J. A.; Yang, J.; Meyer, L. A.; Brozik, J. A. *J. Phys. Chem. A* 2003, 107, 11340-11346; and Yam, V. W.-W. *Acc. Chem. Res.* 2002, 35, 555-563.) Transition metal acetylides are square planar molecules having the molecular formula cis or trans-M(PR$_3$)$_2$ (C≡CR')$_2$. The R' group is typically an aromatic substituent. Common R groups include methyl, ethyl, butyl and phenyl, which all give crystallinity. The transition metal M is selected from the group consisting of palladium, platinum, nickel, and mixtures thereof. Platinum acetylides and the polymeric platinum polyynes (Frazier, C. C.; Guha, S.; Chen, W. U.S. Pat. No. 4,879,479,1989; Friend, R.; Kohler, A. U.S. Pat. No. 5,698,048,1997) have been shown to undergo efficient conversion to a broad band absorbing triplet state upon excitation by a laser. In the prior art, polymeric or oligomeric versions of these compounds containing the tributyl phosphine group, P(C$_4$H$_9$)$_3$ (designated as PBu$_3$) have been described. The palladium acetylide polymer (Frazier, 1989, supra)

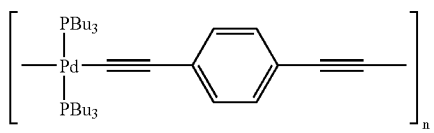

has been shown to have good optical properties, including high optical nonlinearity and high visible transparency and can be used in devices for nonlinear optics, frequency converters for optical computing and communication. The applicants prepared free standing films by dissolving the polymer and Upjohn polyimide 2080D in 1-methyl-2-pyyrolidone. They spread the solution on a glass plate using a doctor blade and following drying in a vacuum oven for 24 hours obtained a film having 25-120 µm thickness. The film has a measured nonlinear refractive index n$_2$ that is 58 times that of carbon disulfide.

The related transition metal polymer (Friend, 1997, supra)

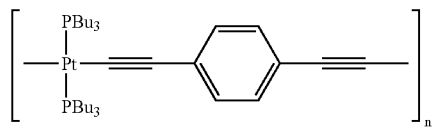

is used as a photoresponsive material combined with a fullerene. The material is placed in a photoresponsive device consisting of indium/tin oxide coated glass substrate, a polymer/fullerene thin film and an aluminum layer. By mixing the polymer with a fullerene, the efficiency of charge generation following photon absorption increases by lengthening the lifetime of an intermediate neutral excited state. This causes crossing to the triplet state and enhances charge separation. The inventors of this patent show that a mixture of the polymer and C$_{60}$ quenches the triplet luminescence and enhances carrier photogeneration by a factor of 1000 over devices made with the polymer alone.

The polymers from the prior art are crystalline and have limited solubility. Unfortunately, the low solubility limits the dye concentration to the millimolar range, thereby decreasing device performance. An example of the prior art is the platinum acetylide complex (abbreviated as PE2).

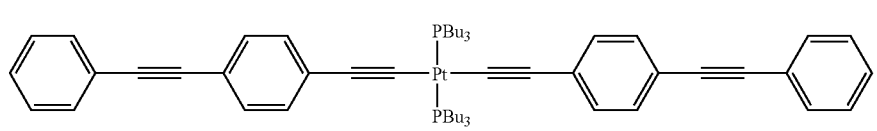

PE2 is a crystalline compound with a melting point of 137° C. (McKay, T. J.; Bolger, J. A.; Staromlynska, J.; Davy, J. R. *J. Chem. Phys.* 1998, 108, 5537-5541). High concentrations are necessary for the study of phenomena like triplet-triplet annihilation, exciton migration and nonlinear optical properties as well as improved performance when used in optical devices. Solubility problems have prevented the study of high concentration solutions of PE2 and related chromophores.

In order to develop methods for lowering the melting point and increasing the solubility of platinum acetylide chromophores, the applicants used trioctyl phosphine as a reagent for the preparation of the platinum acetylide complexes. Trioctyl phosphine has been used as a reagent and a passivating agent in the synthesis of monodisperse semiconductor nanocrystals (Wuister, S. F.; van Houselt, A.; Donega, C.; Vanmaekelbergh, D.; Meijerink, A. *Angew. Chem. Int. Ed.* 2004, 43, 3029-3033). Also, trioctyl phosphine-containing catalysts having one Ru atom bonded to two P atoms, in particular bis(acetylacetonato)bis(phosphine)ruthenium complexes have been prepared (Kawakami, K.; Utsunomiya, M.; Takahashi, K. Japan Patent 2003238579 2003). Surprisingly, the applicants have found that platinum acetylide compounds containing this trioctyl phosphine group ligand are liquids at room temperature, thereby making possible the development of devices requiring materials with a high chromophore concentration.

SUMMARY OF THE INVENTION

The present invention relates to the field of devices for nonlinear optics, frequency conversion, optical switching, photoconductivity, photovoltaics, electroluminescence, pressure-sensitive paint and electrochemical sensor using organometallic compounds.

The organometallic compounds of the present invention are transition metal acetylide complexes having the functional group $P(C_8H_{17})_3$ (designated as $POct_3$) bound to the metal. The molecular formula of these complexes is $M(POct_3)_2(C≡CR)_2$. The transition metal M is selected from the group consisting of palladium, platinum, nickel, and mixtures thereof. R is an organic or organometallic group.

The inventors have discovered that transition metal complexes containing the $POct_3$ group are liquids at room temperature. The thermodynamic properties of these complexes are measured by differential scanning calorimetry. Upon cooling, the liquids convert to glasses in the temperature range −80 to −100° C. Upon heating the glasses convert back to liquids. During heating some of the liquids behave as supercooled liquids and crystallize. The solids then melt to the liquid phase upon heating to room temperature. These materials are superior to prior art transition metal acetylide materials as the chromophores are neat liquids. Importantly, their viscosity is low enough that it is straightforward to pipette the liquid into an optical cell or prepare a thin film. The liquids have a high chromophore number density, enabling their use in optical devices.

These liquids may be used in a variety of forms. The pure compounds can be used as neat liquids or thin films. When mixed with other materials these compounds can be used as liquids, thin films or solid films or doped into a host material. Nonlinear optics applications for these materials include phase conjugation, optical bistability, optical switching, harmonic generation, parametric mixing and oscillation and signal processing. When these materials are coated onto a surface, their phosphorescence is sensitive to the partial pressure of oxygen in the atmosphere. Therefore, they could have application as pressure sensitive paints or as oxygen sensors.

DETAILED DESCRIPTION OF THE INVENTION

Figure 1:
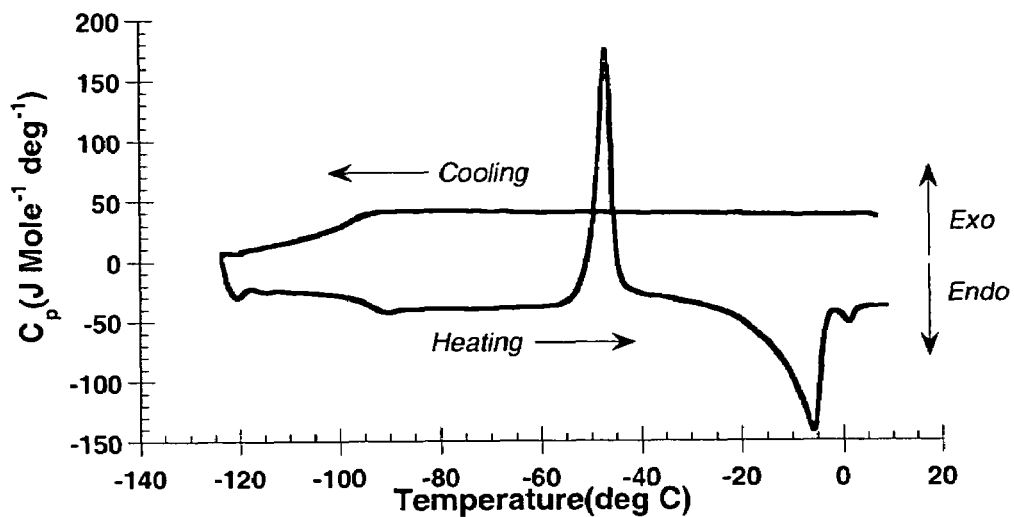
FIG. 1 is the differential scanning calorimeter thermogram of compound 2.

The applicants have discovered a series of platinum acetylides that form a liquid phase at room temperature and converted to glasses upon cooling. The applicants designed the chromophore, in part, by using the basic relation between melting point and thermodynamic parameters (Dearden, J. C. In *Advances in quantitative structure property relationships*; JAI Press, 1999; Vol. 2, 127-135), $$T_m = \frac{\Delta H_m}{\Delta S_m},$$

where $\Delta H_m$ and $\Delta S_m$ are the enthalpy and entropy of melting. The entropy of melting is increased by introducing bulky, flexible ligands and side chains. The applicants synthesized a series of platinum acetylides having the following formula:

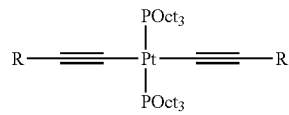

wherein R is an organic or organometallic substituent and $POct_3$ is trioctyl phosphine, having the empirical formula $P(C_8H_{17})_3$.

The platinum acetylides are synthesized according to the reaction scheme:

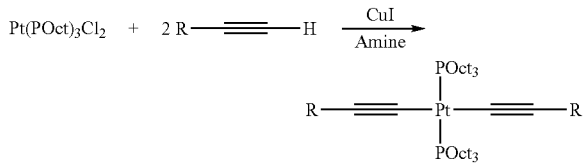

The transition metal acetylides are prepared by a Cadiot-Chodkiewicz coupling reaction. The general reaction and purification procedure involves adding to a microwave cell one equivalent of $PtCl_2(POct_3)_2$, two equivalents of HC≡CR, 0.2 equivalent CuI and $NHEt_2$ (20 ml/meq) and heating for 10 minutes at 150 W [~48 PSI]. After this time the solution is pale green and the white precipitate of $NH_2Et_2Cl$ can be seen seen. Solvent is removed by evaporation. The oily products are dissolved in $CH_2Cl_2$ and purified on alumina. Elution with hexane gives a pale yellow fraction, which yields an oil upon removal of solvent. To eliminate trace amounts of solvent, the purified liquids are gently warmed under a vacuum.

The above reaction scheme was used for the synthesis of the organometallic compounds of the present invention. In one embodiment, the organometallic compounds are linear polymers comprising at least one of the following repeating units:

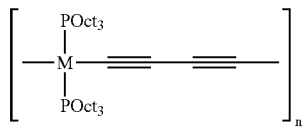

or

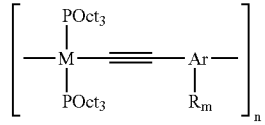

I wherein M is a transition metal; $POct_3$ is the trioctyl phosphine ligand $P(C_8H_{17})_3$; R is an organic substitutent; m is a whole number from 0 to 4; Ar is an aromatic, heterocyclic or organometallic group having from 2 to 60 carbon atoms, oxygen atoms, nitrogen atoms, sulfur atoms, silicon atoms or halogen atoms and mixtures thereof; and n is a whole number from 1 to about 200. The transition metal is selected from the group consisting of palladium, platinum, nickel, and mixtures thereof.

In one preferred embodiment, the linear polymer comprises repeating units of the formula II below:

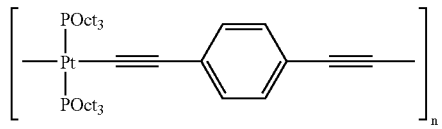

II where n is a whole number from 1 to about 200.

In another preferred embodiment, the organometallic compounds have formula III below:

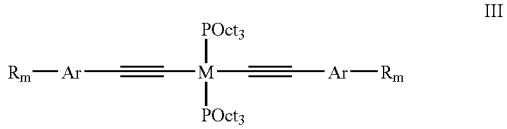

III wherein M is a transition metal; R is an organic substitutent; m is a whole number from 0 to 4; and Ar is an aromatic, heterocyclic or organometallic group having from 2 to 60 atoms selected from the group consisting of carbon atoms, oxygen atoms, nitrogen atoms, sulfur atoms, silicon atoms or halogen atoms, and mixtures thereof.

Preferably, in the organometallic corn pound of formula III above, M is Pt, Ar is a phenyl group and $R_m$ is X, wherein said organometallic compound has the following formula IV:

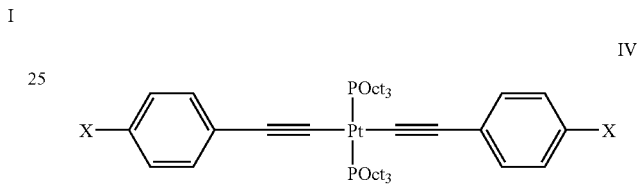

IV wherein X is a an aliphatic, cycloaliphatic, aromatic or heterocyclic group having from 2 to 60 atoms selected from the group consisting of carbon atoms, oxygen atoms, nitrogen atoms, sulfur atoms, silicon atoms or halogen atoms, and mixtures thereof.

Examples of platinum acetylides compounds are listed in Table 1 below:

TABLE I

List of compounds prepared

| Compound | Number |
|---|---|
| $PtCl_2(POct_3)_2$ | 1 |
| $Pt(C\equiv C\ C_6H_5)_2(POct_3)_2$ | 2 |
| $Pt(C\equiv CC_6H_4C\equiv C\ C_6H_5)_2(POct_3)_2$ | 3 |
| $Pt(C\equiv CC_6H_4C_6H_5)_2(POct_3)_2$ | 4 |
| $Pt(C\equiv CC_6H_4Br)_2(POct_3)_2$ | 5 |
| $Pt(C\equiv CC_6H_4C\equiv CC_6H_4C(CH_3)_3)_2(POct_3)_2$ | 6 |
| $Pt(C\equiv CC_6H_4C\equiv CH)_2(POct_3)_2$ | 7 |

A preferred embodiment of the organometallic compound of formula IV above is compound 3 from Table I, wherein said compound has the formula:

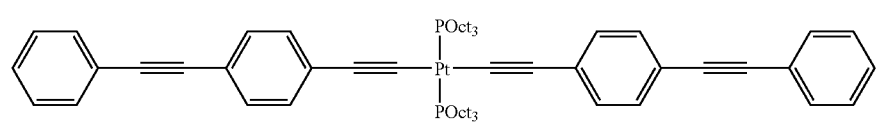

3

Another preferred embodiment of an organometallic compound of formula IV above is organometallic compound 4 from Table I, wherein said compound has the formula:

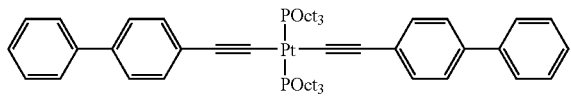

4

Yet another preferred embodiment of an organometallic compound of formula IV above is compound 2 from Table I, wherein said compound has the formula:

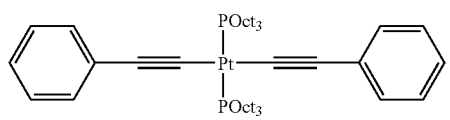

2

The measured % C and % H from combustion elemental analysis of compounds 1-5 and 7 are within 0.4% of the calculated values, showing they are analytically pure. To give similar agreement with compound 6, it is necessary to assume 0.33 moles $CH_2Cl_2$ per mole of compound. Compound 6 has bulky t-Butyl groups attached to the phenyl rings. In 6, trace amounts of the solvent molecules remain tenaciously bound in spite of prolonged heating under vacuum. Surprisingly, applicants have found that compounds containing this trioctyl phosphine group ligand are liquids at room temperature. Importantly, their viscosity is low enough that it is straightforward to pipette the liquid into an optical cell. The compounds remain liquids below room temperature, converting to a glass in the range from about −80° C. to about −100° C. Therefore the neat liquids are easily processable into optical cells and can be used in nonlinear optics applications. Neat liquids have high chromophore concentration (~1-2 M), making possible development of devices requiring high chromophore concentration. The increased chromophore density is shown in compound 3. From a measured density of 1.15 gm/ml, the applicants estimate the chromophore density to be 0.86 moles chromophore/liter of 3. In the prior art, the solubility limit of PE2 has been determined to be 0.08 M (McKay,1998, supra), so use of trioctylphosphine instead of tributylphosphine as the phosphine ligand increases the chromophore number density by a factor of 10.

Figure 2:
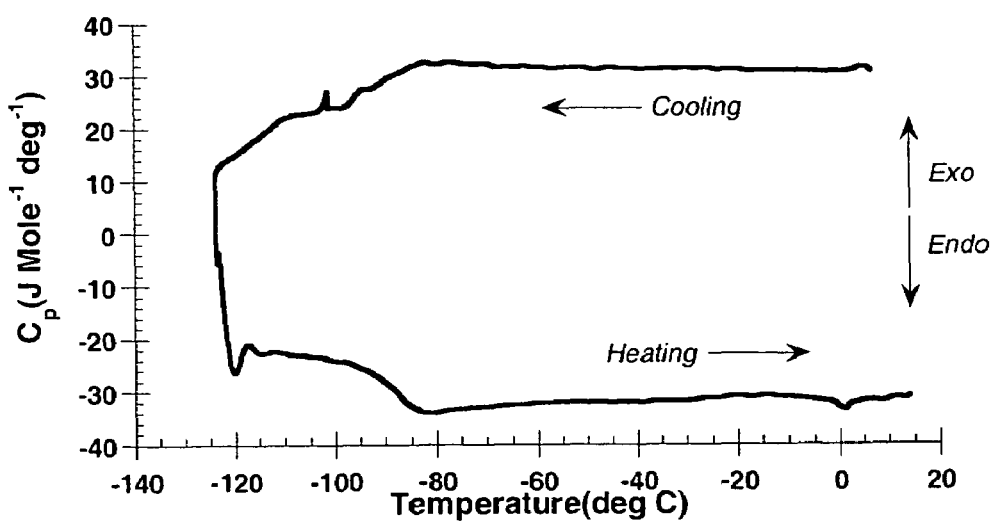
FIG. 2 is the differential scanning calorimeter thermogram for compound 3.

To investigate phase transitions of these compounds, applicants collect DSC thermograms. All of the compounds form glasses upon cooling. Upon heating from the glass, some of the compounds crystallize and then melt to the liquid. An example of this behavior is shown in the thermogram of compound 2 (FIG. 1). It converts to a glass at −90.5° C. Upon heating it converts back to a liquid. At −47.3° C., an exotherm resulting from crystallization appears. With continued heating an endotherm resulting from crystal melting appears at −5.9° C. with no other phase changes at higher temperature. The phase behavior suggests that upon cooling the high viscosity inhibits crystal growth. Upon heating, crystal growth occurs, followed by melting to the liquid phase. Similar behavior has been observed in the intensively-studied glass-forming liquid triphenyl phosphate (Senker, J.; Rossler, E. *Chem. Geol.* 2001, 174, 143-156). In contrast to compound 2, the thermogram for 3 shows no evidence of crystallization from the glass upon heating (FIG. 2). It converts into a glass at −82° C. and reverts back into a liquid upon heating. The glass transition, crystallization and melting temperatures for all the compounds are summarized in Table 2 below.

TABLE 2

Thermal transitions observed in differential scanning calorimetry experiments

| Compound | Number | $T_g^a$ | $T_{exo}^b$ | $T_{endo}^c$ |
|---|---|---|---|---|
| $PtCl_2(POct_3)_2$ | 1 | −70.2 | −26.7 | 4.0 |
| $Pt(C\equiv C\ C_6H_5)_2(POct_3)_2$ | 2 | −90.5 | −47.3 | −5.9 |
| $Pt(C\equiv CC_6H_4C\equiv C\ C_6H_5)_2(POct_3)_2$ | 3 | −82.2 | N/A | N/A |
| $Pt(C\equiv CC_6H_4\ C_6H_5)_2(POct_3)_2$ | 4 | −81.0 | N/A | N/A |
| $Pt(C\equiv CC_6H_4Br)_2(POct_3)_2$ | 5 | −88.2 | −33.1 | 7.9 |
| $Pt(C\equiv CC_6H_4C\equiv CC_6H_4C(CH_3)_3)_2(POct_3)_2$ | 6 | −78.0 | N/A | N/A |
| $Pt(C\equiv CC_6H_4C\equiv CH)_2(POct_3)_2$ | 7 | −67.0 | N/A | N/A |

[a] DSC measurements are performed by equilibrating a weighed sample placed in a sealed aluminum pan at 15° C., cooling at 4° C./min to −120° C., followed by equilibration at −120° C. and heating at 4° C./min to 20° C. The glass transition temperature in 0° C. is measured from the overshoot peak temperature of the heating portion of the thermogram.
[b] No thermal transitions resulting from crystallization were observed during cooling. However, during heating, some of the compounds showed an exotherm resulting from crystallization from the supercooled liquid. The listed $T_{exo}$ in ° C. is the temperature of maximum heat release during the transition.
[c] For those compounds having an exotherm resulting from crystallization during heating, an endotherm resulting from melting the crystals is observed. The listed $T_{endo}$ in ° C. is the temperature of maximum heat uptake during the transition.

Compounds 1, 2 and 5 form glasses upon cooling and crystallize followed by melting upon heating. Compounds 3, 4, 6 and 7 only form glasses and do not crystallize. There appears to be a correlation between ligand size and crystallization behavior. In all the compounds the presence of the trioctylphosphine ligands inhibits crystallization during cooling. The presence of smaller side chains in compounds 1,2 and 5 promote crystallization during heating. The larger side chains in compounds 3, 4, 6 and 7 inhibit crystallization during heating. Literature results have shown a phthalocyanine glass has a glass transition temperature of 65° C. (George, R. D.; Snow, A. W. *Chem. Mater.* 1994, 6, 1587-1588.). Recently, a two-photon absorber is shown to be a glass at room temperature, converting to a fluid upon heating to 70-80° C. (Kannan, R.; He, G. S.; T.-C., L.; Prasad, P. N.; Vaia, R.; Tan, L.-S. *Chem. Mater.* 2004, 16, 185-194).

Glasses have been classified as either "strong" or "fragile" (Angell, C. A. *Chem. Rev.* 2002, 102, 2627-2650). Materials with networks of covalent bonds, like silica, show a small decrease in heat capacity(10-20%) during the glass transition and are classified as "strong" glasses. Materials where weak intermolecular forces (hydrogen bonding, Van der Waals and electrostatic) predominate show a large(~2-fold) drop in heat capacity during the glass transition and are classified as "fragile" glasses. In the compounds described herein, there was an approximately 2-fold drop in heat capacity as the compounds converted to glass, suggesting that they were "fragile" glasses.

Figure 3:
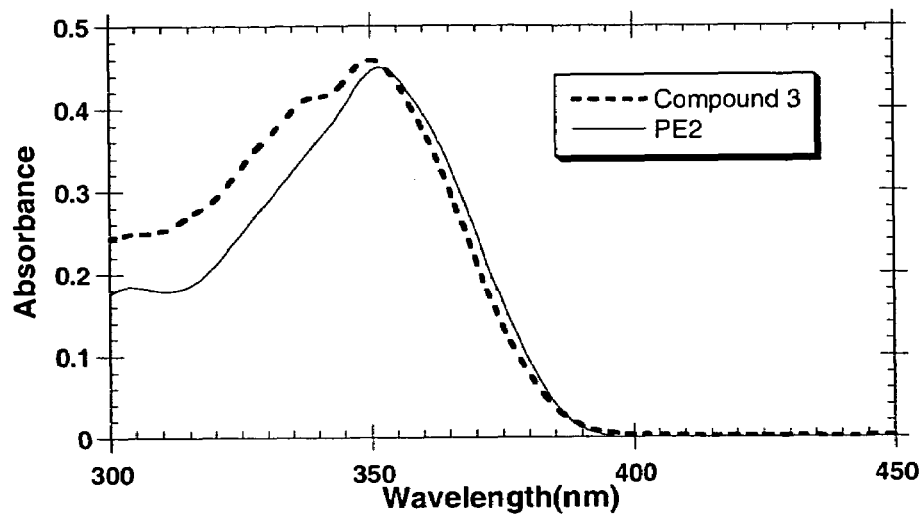
FIG. 3 is the ground state absorption spectrum of compound 3 and PE2.
Figure 4:
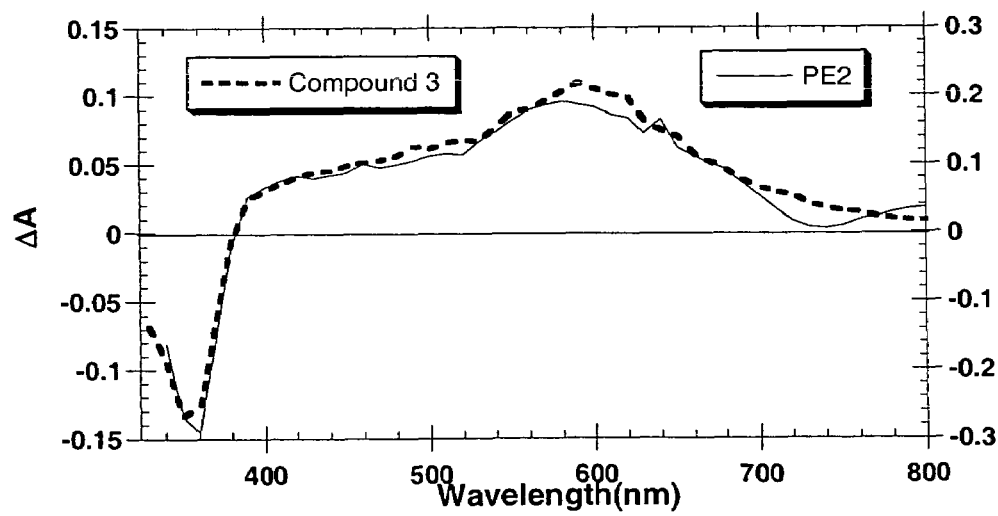
FIG. 4 is the triplet state absorption spectrum of compound 3 and PE2.
Figure 5:
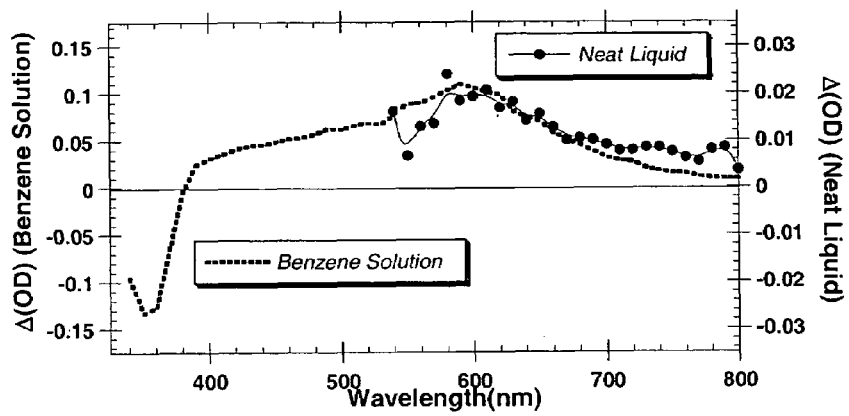
FIG. 5 is the triplet state absorption spectrum of neat liquid compound 3 compared to compound 3 dissolved in benzene.
Figure 6:
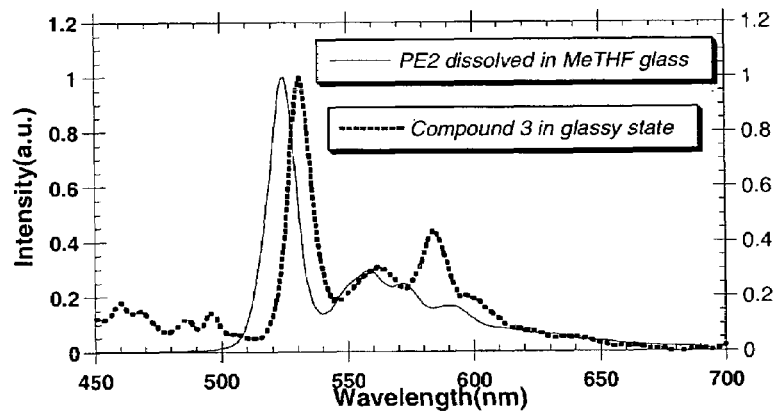
FIG. 6 is the phosphorescence spectrum of compound 3 in a glassy state compared with phosphorescence spectrum of PE2 dissolved in a MeTHF glass.

An example of the excited state properties of these liquids is shown in a flash photolysis experiment on compound 3. Nanosecond transient absorption measurements are carried out using the third harmonic (355-nm) of a Q-switched Nd:YAG laser (Quantel Brilliant, pulse width ca. 5 ns). Pulse fluences of up to 8 mJ cm-2 at the excitation wavelength are typically used. A detailed description of the laser flash photolysis apparatus has been published (Rogers, 2002, supra). Compound 3 is closely related to PE2. Upon optical excitation, PE2 undergoes a mixed $\pi\pi^*$-metal-to-ligand charge transfer transition to an $S_1$ excited state localized on the aromatic ligand. The heavy atom effect of the platinum promotes rapid conversion to the triplet state. The transient absorption spectrum has been shown to be that of the triplet state (Rogers, 2002, supra) The ground state absorption spectrum of dilute 3 and the triplet state absorption spectrum are identical to the spectra of a dilute solution of PE2 (FIGS. 3 and 4), showing substituting the ligand trioctylphosphine for tributylphosphine has no effect on 3's conversion to the triplet state in dilute solution. The excited state behavior of dilute 3 is compared vs. the neat liquid (FIG. 5). Chromophore 3 was diluted in benzene to an OD(355 nm)=0.43, degassed by freeze-pump-thaw and the excited at 355 nm. The triplet state spectrum of the solution was calculated from fitting the decay data and extrapolating to t=0 sec. The neat liquid 3 was air saturated and excited at 520 nm. The data shown were collected 0.603 μsec after excitation. The triplet state of degassed, dilute 3 shows single exponential decay with a lifetime of 83 μsec, in good agreement with the 42 μsec lifetime of degassed, dilute PE2 (Rogers, 2002, supra). The triplet state of air-saturated, neat 3 shows biexponential decay with a fast lifetime of 26 nsec and a slow lifetime of 1.2 μsec. The fast decay may have resulted from oxygen quenching, ground state quenching or triplet-triplet annhilation. The slow lifetime is longer than the lifetime of air-saturated, dilute PE2 (240 nsec), resulting from the higher viscosity of 3. To measure phosphorescence from the glassy state, compound 3 or PE2 dissolved in MeTHF was placed in a quartz capillary and cooled to 77° K. Emission spectra were collected by exciting the sample at 350 nm. The spectrometer excitation and emission slit widths were set at 5 nm. Neat 3 was cooled to 77° K. and upon irradiation with UV light, a phosphorescence spectrum was obtained that is similar to that of PE2 dissolved in a glass-forming solvent (FIG. 6).

In the present invention, applicants have described a series of platinum acetylide complexes that are liquids at room temperature and form glasses upon cooling. Importantly, the series of platinum acetylide complexes shown a tenfold increase in chromophore density in compound 3 compared to a saturated solution of PE2. By increasing the number density, it is possible to increase the magnitude of the nonlinear coefficient $\chi^{(3)}$. Because of the high concentration, it is feasible to measure nonlinear optical properties like two photon absorption spectra (Goodman, L.; Rava, R. P. *Acc. Chem. Res.* 1984, 17, 250-257). These compounds can be used in devices for nonlinear optics, frequency conversion, optical switching, photoconductivity, photovoltaics, electroluminescence, pressure-sensitive paint and electrochemical sensor using organometallic materials.

EXAMPLE 1

Synthesis of $PtCl_2(POct_3)_2$

To a solution of $K_2[PtCl_4]$ (2000 mg, 4.84 mmol) in water (50 ml) trioctylphosophine (4313 μl, 9.68 mmol) was added and the resulting solution left to stir at room temperature for 2 days giving a yellow sticky solid. Dichloromethane (30 ml) was added and the organic layer separated. Removal of the solvent gave a yellow liquid, which crystallises upon cooling. Identified as a mixture of cis- and trans- $PtCl_2(POct_3)_2$ 1 (3000 mg, 62%). MA: found C, 57.54; H, 10.08. $C_{48}H_{102}Cl_2P_2Pt$. requires C, 57.24; H, 10.21%. $M_w$=1005. $^1$H NMR ($CDCl_3$): 80.88 (m, 3H, $CH_3$), 1.25 (m, 8H, $CH_2$), 1.38 (m, 2H, $CH_2$), 1.52 (m, 2H, $CH_2$), 1.95 (m, 2H, $CH_2$) ppm. $^{13}$C NMR ($CDCl_3$): δ 14.30 (s, $CH_3$), 22.85 (s, $CH_2$), 24.38 (t, J(CP)=17 Hz, $CH_2$), 24.70 (s, $CH_2$), 29.41 (s, $CH_2$), 29.45 (s, $CH_2$), 31.30 (t, J(CP)=7 Hz, $CH_2$), 32.05 (s, $CH_2$) ppm. $^{31}$P NMR ($CDCl_3$): δ 2.08 (s, J(PPt)=3515 Hz, cis-$POct_3$), 5.75 (s, J(PPt)=2378 Hz, trans-$POct_3$) ppm. El MS: (m/z) 1005, [M]$^+$; 935, [M-2Cl]$^+$; 407, [Cl.P($C_8H_{17}$)$_3$]$^+$; 371, [H.P($C_8H_{17}$)$_3$]$^+$; 258, [H.P($C_8H_{17}$)$_2$]+.

EXAMPLE 2

Synthesis of $Pt(C\equiv CPh)_2(POct_3)_2$

To a microwave cell, $PtCl_2(POct_3)_2$ (500 mg, 0.50 mmol), $HC\equiv CPh$ (137 μl, 1.24 mmol), CuI (19 mg, 0.1 mmol) and $NHEt_2$ (10 ml) were added and heated for 10 minutes at 150 W [~48 PSI]. After this time the solution was pale green and the white precipitate of $NH_2Et_2Cl$ was seen. Solvent was removed, residue dissolved in $CH_2Cl_2$ and purified on alumina, elution with hexane gave a pale yellow fraction, which gave an oil upon removal of solvent. Identified as $Pt(C\equiv CPh)_2(POct_3)_2$ (512 mg, 90%). MA: found C, 67.58; H, 9.96. $C_{64}H_{112}P_2Pt$ requires C, 67.51; H, 9.91%. $M_w$=1137.79. $^1$H NMR ($CDCl_3$): δ 0.89 (m, 3H, $CH_3$), 1.27 (m, 8H, $CH_2$), 1.42 (m, 2H, $CH_2$), 1.60 (m, 2H, $CH_2$), 2.16 (m, 2H, $CH_2$), 7.10-7.29 (m, 5H, ArH) ppm. $^{13}$C NMR ($CDCl_3$): δ14.38 (s, $CH_3$), 22.94 (s, $CH_2$), 24.38 (t, J(CP) =17 Hz, $CH_2$), 24.48 (s, $CH_2$), 29.51 (s, $CH_2$), 31.59 (t, J(CP)=7 Hz, $CH_2$), 32.16 (s, $CH_2$), 108.28 (t, J(CP)=15 Hz, Pt—C≡C), 109.20 (s, Pt—C—C), 124.98 (s, ArH), 128.01 (s, ArH), 129.35 (s, Ar), 131.06 (s, ArH) ppm. $^{31}$P NMR ($CDCl_3$): δ 4.41 (s, J(PPt)=2355 Hz, $POct_3$) ppm. El MS: (m/z) 1138, [M]$^+$; 1024, [M—$C_8H_{17}$]$^+$; 558, [Pt(PC$_8$H$_{15}$)$_2$]$^+$; 471, [PhC≡C.P($C_8H_{17}$)$_3$]$^+$; 371, [H.P($C_8H_{17}$)$_3$]$^+$. ES MS: (added NaOMe, m/z) 1160, [M+Na]$^+$.

EXAMPLE 3

Synthesis of $Pt(C\equiv CC_6H_4C\equiv CPh)_2(POct_3)_2$

To a solution of $PtCl_2(POct_3)_2$ (200 mg, 0.20 mmol) and $HC\equiv CC_6H_4C\equiv CPh$ (100 mg, 0.50 mmol) in a mixture of piperidine (5 ml) and toluene (10 ml), CuI (4 mg, 0.02 mmol) was added and stirred at room temperature for 16 hours. Solvent was removed and the residue was dissolved in CH$_2$Cl$_2$ and purified on alumina, elution with hexane gave an orange-yellow fraction, which gave an orange-yellow oil upon removal of solvent. Identified as Pt(C≡CC$_6$H$_4$C≡CPh)$_2$(POct$_3$)$_2$ (454 mg, 85%). MA: found C, 71.78; H, 8.80. C$_{80}$H$_{120}$P$_2$Pt requires C, 71.77; H, 9.03%. M$_w$=1337.85. $^1$H NMR (CDCl$_3$): δ 0.90 (m, 3H, CH$_3$), 1.28 (m, 8H, CH$_2$), 1.43 (m, 2H, CH$_2$), 1.65 (m, 2H, CH$_2$), 2.15 (m, 2H, CH$_2$), 7.24-7.55 (m, 9H, ArH) ppm. $^{13}$C NMR (CDCl$_3$): δ 14.41 (s, CH$_3$), 22.97 (s, CH$_2$), 24.38 (t, J(CP)=17 Hz, CH$_2$), 24.50 (s, CH$_2$), 29.53 (s, CH$_2$), 31.60 (t, J(CP)=7 Hz, CH$_2$), 32.18 (s, CH$_2$), 89.98 (s, C—C), 90.33 (s, C≡C), 109.66 (s, Pt—C—C), 112.04 (t, J(CP)=15 Hz, Pt—C≡C), 123.86-132.69 (m, Ar and ArH) ppm. $^{31}$P NMR (CDCl$_3$): δ 4.51 (s, J(PPt)=2342 Hz, POct$_3$) ppm. El MS: (m/z) 1338, [M]$^+$; 935, [Pt(P(C$_8$H$_{17}$)$_3$)$_2$]$^+$; 573, rPhC≡CC$_6$H$_4$C≡C.P(C$_8$H$_{17}$)$_3$+2H]$^+$; 571; [PhC≡CC$_6$H$_4$C≡C.P(C$_8$H$_{17}$)$_3$]$^+$; 369, [P(C$_8$H$_{17}$)$_3$—H]$^+$; 327, [C$_5$H$_{10}$P(C$_8$H$_{17}$)$_2$]$^+$; 285, [C$_2$H$_5$P(C$_8$H$_{17}$)$_2$]$^+$; 228, HP(C$_8$H$_{17}$)$_2$)$^+$. ES MS: (added NaOMe, m/z) 1360, [M+Na]$^+$.

EXAMPLE 4

Synthesis of Pt(C≡CC$_6$H$_4$Ph)$_2$(POct$_3$)$_2$

To a microwave cell, PtCl$_2$(POct$_3$)$_2$ (500 mg, 0.50 mmol), HC≡CC$_6$H$_4$Ph (196 mg, 1.10 mmol), CuI (10 mg, 0.05 mmol) and NHEt$_2$ (15 ml) were added and heated for 30 minutes at 150 W [~48 PSI]. After this time the solution was pale green and the white precipitate of NH$_2$Et$_2$Cl was seen. Solvent was removed, residue dissolved in CH$_2$Cl$_2$ and purified on alumina, elution with hexane gave a pale yellow fraction, which gave a yellow oil upon removal of solvent. Identified as Pt(C≡CC$_6$H$_4$Ph)$_2$(POct$_3$)$_2$ (305 mg, 48%). MA: found C, 70.77; H, 9.42. C$_{76}$H$_{120}$P$_2$Pt requires C, 70.72; H, 9.37%. M$_w$=1289.85. $^1$H NMR (CDCl$_3$): δ0.88 (m, 3H, CH$_3$), 1.28 (m, 8H, CH$_2$), 1.46 (m, 2H, CH$_2$), 1.67 (m, 2H, CH$_2$), 2.17 (m, 2H, CH$_2$), 7.35-7.62 (m, 9H, ArH) ppm. $^{13}$C NMR (CDCl$_3$): δ 14.39 (s, CH$_3$), 22.95 (s, CH$_2$), 24.45 (t, J(CP)=17 Hz, CH$_2$), 24.53 (s, CH$_2$), 29.55 (s, CH$_2$), 31.64 (t, J(CP)=7 Hz, CH$_2$), 31.87 (s, CH$_2$), 32.19 (s, CH$_2$), 109.18 (s, Pt—C≡C), 109.71 (t, J(CP)=15 Hz, Pt—C≡C), 126.76 (s, ArH), 126.99 (s, ArH), 127.09 (s, Ar), 128.93 (s, ArH), 131.44 (s, ArH), 137.64 (s, Ar), 141.42 (s, Ar) ppm. $^{31}$P NMR (CDCl$_3$): δ 4.50 (s, J(PPt)=2353 Hz, POct$_3$) ppm.

Having thus described exemplary embodiments of the present invention, it should be noted by those skilled in the art that the disclosures herein are exemplary only and that alternatives, adaptations and modifications may be made within the scope of the present invention.

What is claimed is:

1. An organometallic compound having the formula:

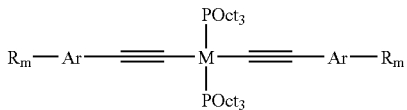

wherein M is a transition metal; R is an organic substitutent; m is a whole number from 0 to 4; and Ar is an aromatic, heterocyclic or organometallic group having from 2 to 60 atoms selected from the group consisting of carbon atoms, oxygen atoms, nitrogen atoms, sulfur atoms, silicon atoms, halogen atoms and mixtures thereof.

2. The organometallic compound of claim 1 wherein said compound has the formula:

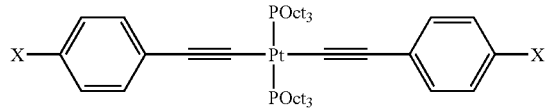

wherein X is a an aliphatic, cycloaliphatic, aromatic or heterocyclic group having from 2 to 60 atoms selected from the group consisting of carbon atoms, oxygen atoms, nitrogen atoms, sulfur atoms, silicon atoms, halogen atoms and mixtures thereof.

3. The organometallic compound of claim 2 wherein said compound has the formula:

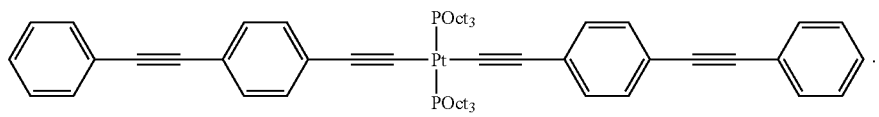

4. The organometallic compound of claim 2 wherein said compound has the formula:

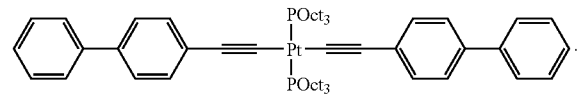

5. The organometallic compound of claim 2 wherein said compound has the formula:

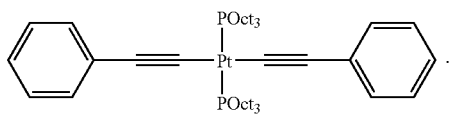

* * * * *